United States Patent [19]

Clarke et al.

[11] Patent Number: 5,168,322

[45] Date of Patent: Dec. 1, 1992

[54] SURFACE INSPECTION USING RETRO-REFLECTIVE LIGHT FIELD

[75] Inventors: Donald A. Clarke; Rodger L. Reynolds; Timothy R. Pryor, all of Windsor, Canada

[73] Assignee: Diffracto Ltd., Windsor, Canada

[21] Appl. No.: 747,903

[22] Filed: Aug. 19, 1991

[51] Int. Cl.⁵ .................. G01N 21/88; G01B 11/30
[52] U.S. Cl. .................... 356/237; 250/572; 356/394
[58] Field of Search ............... 356/237, 445, 394; 250/563, 571, 572

[56] References Cited

U.S. PATENT DOCUMENTS

| | | |
|---|---|---|
| 1,998,054 | 4/1935 | McBurney . |
| 2,798,966 | 7/1957 | Summerhayes, Jr. . |
| 3,019,346 | 1/1962 | Laycak . |
| 3,279,313 | 10/1966 | Kowalik et al. . |
| 3,439,988 | 4/1969 | Breske . |
| 3,590,258 | 6/1971 | Shibata et al. . |
| 3,594,087 | 7/1971 | Miranda ...................... 250/571 X |
| 3,666,370 | 5/1972 | Seasholtz . |
| 3,667,846 | 6/1972 | Nater et al. . |
| 3,702,213 | 11/1972 | Schwab . |
| 3,734,626 | 5/1973 | Roberts et al. . |
| 3,767,306 | 10/1973 | Mast et al. . |
| 3,782,836 | 1/1974 | Fey et al. ..................... 356/237 X |
| 3,794,427 | 2/1974 | Shibata et al. ................ 356/237 X |
| 3,797,943 | 3/1974 | Nagao et al. ................. 356/237 X |
| 3,814,945 | 6/1974 | Allnutt et al. .................. 250/571 |
| 3,857,637 | 12/1974 | Obenreder .................... 356/237 X |
| 3,866,038 | 2/1975 | Korth ............................ 250/563 X |
| 3,871,771 | 3/1975 | Scott . |
| 3,879,989 | 4/1975 | Brenden . |
| 3,892,494 | 7/1975 | Baker et al. .................. 356/239 |
| 3,917,957 | 11/1975 | Ansevin et al. ............... 250/573 |

(List continued on next page.)

FOREIGN PATENT DOCUMENTS

| | | |
|---|---|---|
| 0152894 | 8/1985 | European Pat. Off. . |
| 2439988 | 3/1976 | Fed. Rep. of Germany . |
| 3335130 | 4/1985 | Fed. Rep. of Germany . |
| 58-75049 | 5/1983 | Japan . |
| 58-169012 | 10/1983 | Japan . |
| 6150044 | 8/1984 | Japan . |
| 1461866 | 1/1977 | United Kingdom . |
| 2054835 | 2/1981 | United Kingdom . |
| 2095398 | 9/1982 | United Kingdom . |
| 2117897 | 10/1983 | United Kingdom . |
| 2118304 | 10/1983 | United Kingdom . |
| 2133871 | 8/1984 | United Kingdom . |
| 2159271 | 11/1985 | United Kingdom . |
| 84/02398 | 6/1984 | World Int. Prop. O. . |
| 87/00629 | 1/1987 | World Int. Prop. O. . |
| 87/07383 | 12/1987 | World Int. Prop. O. . |

OTHER PUBLICATIONS

V. Bolhouse, "Machine Vision Automates Inspection of Thick-Film Hybrids", IEEE Circuits and Devices Magazine, pp. 44-48, Jan. 1986.

D. Craig, "Potential Applications for Focatron Idea", Nov. 9, 1961.

J. Hecht, "Light Modulators Help Crunch Image Data", High Technology, pp. 69-72, Jan. 1985.

Technical Paper, Society of Manufacturing Engineers, "High Speed Measurement of Fasteners for Quality Control", 1983. by North et al.

W. Pastorius, "Gaging and Inspection in the Industrial Environment Through The Use of Robot Vision", pp. 7-56-7-66.

J. Walker, "The Amateur Scientist", Scientific American, pp. 118-124, Nov. 6, 1987.

V. Wolanski, "Vision System Senses Needs of Sheetmetal Fabrication", Machine and Tool Blue Book, pp. 62-64, Dec. 1984.

*Primary Examiner*—Vincent P. McGraw
*Attorney, Agent, or Firm*—Larson and Taylor

[57] ABSTRACT

This invention relates to an electro-optical technique which senses form type and other defects on surfaces such as sheet metal or plastic panels. Method and apparatus are disclosed for allowing the inspection of the entire surface of interest from a single point of view while reducing the complexity of defects' optical signatures to simplify their subsequent analysis.

14 Claims, 1 Drawing Sheet

U.S. PATENT DOCUMENTS

| | | | |
|---|---|---|---|
| 3,976,382 | 8/1976 | Westby | 356/237 X |
| 4,130,361 | 12/1978 | Humphrey | 356/125 |
| 4,172,666 | 10/1979 | Clarke | 356/432 |
| 4,207,467 | 6/1980 | Doyle | 250/391 |
| 4,218,144 | 8/1980 | Whitehouse et al. | 356/446 |
| 4,305,661 | 12/1981 | Pryor et al. | 356/241 |
| 4,310,242 | 1/1982 | Genco et al. | 356/128 |
| 4,326,808 | 4/1982 | Pryor et al. | 356/445 |
| 4,389,669 | 6/1983 | Epstein et al. | 358/101 |
| 4,394,683 | 7/1983 | Liptay-Wagner et al. | 358/107 |
| 4,455,086 | 6/1984 | West et al. | 356/237 |
| 4,512,183 | 4/1985 | Alexander | 356/445 X |
| 4,567,769 | 2/1986 | Barkhoudarian | 73/643 |
| 4,581,939 | 4/1986 | Takahashi | 73/643 |
| 4,612,797 | 9/1986 | Barkhoudarian | 73/40.5 R |
| 4,629,319 | 12/1986 | Clarke et al. | 356/237 |
| 4,686,374 | 8/1987 | Liptay-Wagner et al. | 250/571 |
| 4,863,268 | 9/1989 | Clarke et al. | 356/237 |
| 4,907,888 | 3/1990 | Clarke et al. | 356/371 |
| 5,074,661 | 12/1991 | Reynolds et al. | 356/237 |

SURFACE INSPECTION USING RETRO-REFLECTIVE LIGHT FIELD

BACKGROUND OF THE INVENTION

In the course of practicing the invention disclosed in U.S. Pat. No. 4,629,319, which is herein incorporated by reference, we have found certain liabilities to the embodiments of FIGS. 6, 7, and 8a thereof (wherein an area of, in general, a substantial portion of an object is illuminated). These liabilities limit the total area of the surfaces which can be imaged and complicate the detection and analysis of defects. They are unavoidable by-products of the optical apparatus configuration disclosed in the referenced invention.

SUMMARY OF THE INVENTION

The general field of application of this invention applies primarily to inspection of objects such as auto body parts, aircraft panels, appliance surfaces, etc. for cosmetic or functional defects on exterior or other surfaces which need to present a uniformly contoured appearance which is free of localized defects in form. The embodiments of the invention of FIGS. 6, 7 and 8A of the referenced patent are extremely powerful in analyzing such defects.

As it is typically configured, the apparatus of the referenced patent produced images in which localized variations in surface curvature are presented as grey scale changes over most of the illuminated surface. However, the use of so-called off-axis lighting creates two undesirable side-effects. These effects are: 1) inability to inspect the leading and trailing edge (with respect to the imaging system) of the inspected surface, and 2) complex defect signatures consisting of two superimposed optical phenomena which complicate their detection and analysis. The embodiments disclosed herein address these side-effects.

BRIEF DESCRIPTION OF THE DRAWINGS

This invention is illustrated in the following embodiments.

DETAILED DESCRIPTION OF THE PREFERRED EMBODIMENTS

Figure 1:
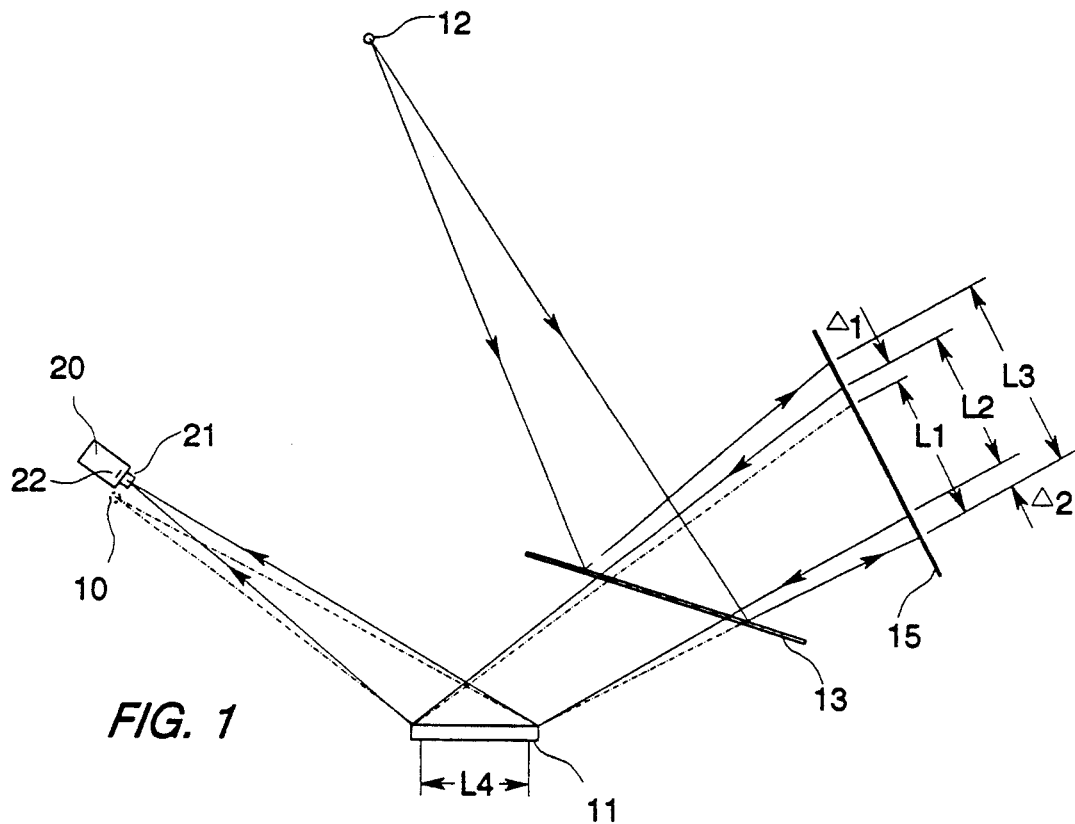
FIG. 1 illustrates the use of a beam-splitter and isolated light-source to image the entire area of a flat surface and eliminate the primary signatures of any defects therein.

FIG. 1 shows a ray-tracing side view of a typical apparatus as disclosed in U.S. Pat. No. 4,629,319 as well as the improved embodiment. In the typical configuration referred to as configuration A, light source 10; illuminates the flat surface 11, strikes retro-reflective screen 15 and is retro-reflected thereby, and is re-reflected via surface 11 to camera 20 comprising lens 21 and, in this example, matrix photo detector 22. Alternatively, other detectors can be used, for example, photographic film, vidicons, mechanically swept linear arrays, mechanically raster scanned infra-red detectors, etc.

In configuration A the light reflected by the surface illuminates an area on the screen whose vertical length is denoted by L1. Due to the camera's location above the lamp, it images an area on the screen, as reflected through the surface, whose vertical length is denoted by L2. Since L2 is not coincident with L1 there is a region on the screen, denoted by length $\Delta 1$, which the camera images but is not illuminated by light reflected from the surface. For this reason, the camera always images a darkened region along the edge of the surface nearest the camera. Similarly, the region on the screen denoted by length $\Delta 2$ represents an area on the screen which is illuminated by light reflected from the surface but is not imaged by the camera. Hence the camera cannot inspect the edge of the surface farthest from it. The first limitation to the configuration A shown is that although the entire surface is illuminated, only the surface region denoted by length L4 is inspected.

If the surface contained a localized curvature defect it has two optical signatures. The first-pass signature, coined the primary, is formed on the screen by the defect slopes causing rays from the light source to converge and diverge, producing brighter and darker regions within the on-screen light field. The second-pass signature, coined the secondary, is formed by the defect slopes causing the camera to image different intensities from the cumulative response of the retro-reflecting elements (e.g. spheres) which comprise the screen (e.g. 3M, Scotchlite ®). When inspecting sheet metal for defects such as dings and dents, each defect is seen as these two signatures superimposed. It has been found that the presence of the primary signatures can complicate their automatic detection and severity analysis. Therefore, it would be desirable if the primary signatures could be eliminated and the entire surface could be inspected.

To achieve these ends, in configuration B, the light source 10 is removed. Light from an "isolated" source 12 reflects from beam-splitter 13 and illuminates the screen over a region denoted by vertical length L3. Assuming the beam-splitter has no significant form errors which could form any primary signatures of their own and that radiation emitted by source 12 travels an equal distance to the screen as that from source 10, the rays forming the light field on the screen will have the same angular distribution (uniform intensity) as if the light had been reflected from an unflawed surface of interest from source 10 along an axis offset from the imaging axis of camera 20. The screen then retro-reflects this light through the beam-splitter wherein it is re-reflected via surface 11 to the camera 20. Since the beam-splitter can be made larger than surface 11, region L3 will totally encompass region L2, ensuring that the camera sees the entire surface illuminated by light reflected from the screen. Hence a localized curvature defect, at any point on the surface, will have only a secondary signature, assuming it contains sufficient slope variations. In many cases the configuration B results in a clear advantage leading to simpler image analysis.

Figure 2:
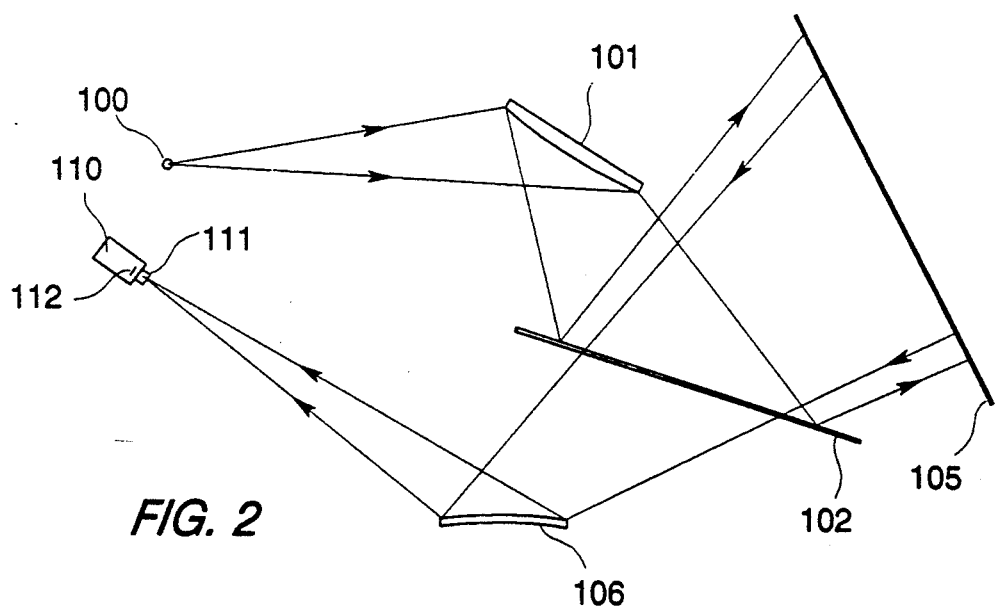
FIG. 2 illustrates the use of a beam-splitter, a reflective master part and an isolated light source to image the entire area of a curved surface and eliminate the primary signatures of any defect therein.

FIG. 2 illustrates an embodiment similar to that shown in FIG. 1 to allow the inspection of the entire area of a curved surface. Light source 100 illuminates a master surface 101 such that the light reflected from surface 101 strikes and reflects from beam-splitter 102 wherein the light strikes retro-reflective screen 105. The light then passes through the beam-splitter wherein it is reflected via surface 106 to be tested to camera 110 comprising lens 111 and matrix photo detector 112. As with the embodiment of FIG. 1, the axis of light from light source 100 is slightly offset from the viewing of imaging axis of camera 110.

Surface 101 is termed a master surface since it represents the shape of the "perfect" surface of test surface 106 with no localized curvature defects. Master surface 101 would have to be a highly reflective, accurately formed representation of the test surface 106 derived from the original design data, whether this be mathematical CAD data or CMM data from a clay model. As well, master surface 101 must be somewhat larger than the true surface 106 of interest so that a sufficiently large light field is formed on the screen. As an accurate reproduction of the test surface, it should be appreciated that the light field formed will contain intensity variations which would correspond to those which would be produced by a primary pass signature of a perfect test surface. The success of this technique is very dependent on accurate fixturing to maintain the correct path lengths and angularity. Once again proper execution of this invention will produce an image of a curved surface wherein the entire surface is inspected and any defect containing sufficient curvature variations therein will have only a secondary signature.

What is claimed is:

1. A method of inspecting a flat surface comprising the steps of:
   illuminating a retro-reflective screen with light reflected from a beam splitter;
   imaging with an image sensor the light from the screen which passes through the beam splitter and is then reflected from the flat surface; and
   determining, from the image detected by the image sensor, a condition of the flat surface.

2. A method of inspecting as claimed in claim 1 wherein said imaging step includes the step of locating an axis of imaging of the image sensor at an angular displacement from an axis of the light reflected from the surface such that bright or dark regions characteristic of form defects on the surface are formed in the image detected.

3. A method of inspecting as claimed in claim 1 wherein said illuminating step includes the step of forming a light field on the screen with the light reflected from the beam splitter which is sufficiently large so that the image sensor images an entire area of the surface with the light from the screen.

4. A method of inspecting as claimed in claim 1 wherein said illuminating step includes the step of forming a light field on the screen with the light reflected from the beam splitter which is of uniform intensity by use of a high quality, flat beam splitter.

5. A method of inspecting a curved surface comprising the steps of:
   illuminating a retro-reflective screen with light reflected first from a curved master surface and thence from a beam splitter;
   imaging with an image sensor the light from the screen which passes through the beam splitter and is then reflected from the curved surface; and
   determining, from the image detected by the image sensor, a condition of the curved surface.

6. A method of inspecting as claimed in claim 5 wherein said imaging step includes the step of locating an axis of imaging of the image sensor at an angular displacement from an axis of the light reflected from the curved surface such that bright or dark regions characteristic of form defects on the curved surface are formed in the image detected.

7. A method of inspecting as claimed in claim 5 wherein said illuminating step includes the step of forming a light field on the screen with the light reflected from the beam splitter which is sufficiently large so that the image sensor images an entire area of the curved surface with the light from the screen.

8. A method of inspecting as claimed in claim 5 wherein said illuminating step includes the step of forming a light field on the screen with the light reflected from the beam splitter which contains intensity variations which are indicative of a perfect shape of the curved surface.

9. An apparatus for inspecting a surface comprising:
   a source of light;
   a retro-reflective screen;
   a beam splitter means provided between the surface and the screen for directing a portion of the light from the light source to the retro-reflective screen to form a light field; and
   an imaging means for imaging the surface with light from the light field which passes back through said beam splitter means from said screen and is reflected from the surface whereby a condition of the surface is determined by the surface image.

10. An apparatus for inspecting as claimed in claim 9 wherein the light from said surface is directed substantially along an axis and said imaging means images along an axis which is angularly displaced from the axis of the light such that bright or dark regions characteristic of form defects on the surface are formed in the image detected.

11. An apparatus for inspecting as claimed in claim 9 wherein the light field formed by said beam splitter means is sufficiently large so that said imaging means images an entire area of the surface with the light from the light field.

12. An apparatus for inspecting as claimed in claim 9 wherein the surface is flat and said light field is of uniform intensity.

13. An apparatus for inspecting as claimed in claim 9 wherein the surface is curved and further including a curved master surface positioned such that the light from said light source is initially reflected therefrom and then to said beam splitter means.

14. An apparatus for inspecting as claimed in claim 13 wherein said curved master surface is indicative of a defect free desired surface of the curved surface such that said light field contains intensity variations which are indicative of a perfect shape of the curved surface.

* * * * *